United States Patent [19]

Daniel et al.

[11] 4,331,813

[45] May 25, 1982

[54] PROCESS FOR MAKING ESTERS OF UNSATURATED ACIDS

[75] Inventors: Chelliah Daniel; Phillis L. Brusky, both of Columbus, Ohio

[73] Assignee: Ashland Oil, Inc., Ashland, Ky.

[21] Appl. No.: 232,605

[22] Filed: Feb. 9, 1981

[51] Int. Cl.$^3$ .................... C07C 67/08; C07C 67/317
[52] U.S. Cl. ...................... 560/205; 560/214
[58] Field of Search ............... 560/214, 205, 210, 211

[56] References Cited

U.S. PATENT DOCUMENTS

| | | | |
|---|---|---|---|
| 2,744,928 | 5/1956 | Smith et al. | 560/205 |
| 3,442,934 | 5/1969 | Pine et al. | 560/205 |
| 3,442,935 | 5/1969 | Pine et al. | 560/205 |
| 3,634,434 | 1/1972 | Tsu | 560/214 |
| 3,644,497 | 2/1972 | Mesich | 560/205 |
| 3,766,191 | 10/1973 | Cichowski . | |
| 3,784,483 | 1/1974 | Cichowski | 252/437 |
| 3,862,910 | 1/1975 | Cichowski | 252/435 |
| 3,948,959 | 4/1976 | Cavaterri et al. | 252/437 |
| 4,212,767 | 7/1980 | Daniel | 252/435 |

Primary Examiner—Natalie Trousof
Assistant Examiner—L. Hendriksen
Attorney, Agent, or Firm—Robert J. Grassi

[57] ABSTRACT

Methyl methacrylate or other $\alpha$-$\beta$ unsaturated esters are prepared by contacting an oxydehydrogenation-esterification catalyst with a feed mixture of a saturated acid (e.g., isobutyric acid), an alkyl alcohol (e.g., methanol), oxygen, with or with $H_2O$, preferably with $H_2O$ for a time sufficient to form an alkyl $\alpha$-$\beta$ unsaturated ester as described herein.

25 Claims, No Drawings

PROCESS FOR MAKING ESTERS OF UNSATURATED ACIDS

BACKGROUND OF THE INVENTION

1. Field of the Invention

The invention relates to catalytic formation of alkyl α-β unsaturated esters from alkyl saturated acids and alkyl alcohols, in particular, the conversion of methanol and isobutyric acid to methyl methacrylate.

2. Description of the Prior Art

The prior art generally describes the catalytic oxydehydrogenation of alkyl saturated acids to alkyl unsaturated acids which are then separated and esterified. Some art describes the catalytic oxydehydrogenation of alkyl saturated esters. The art, however, is silent concerning the formation of alkyl esters of alkyl α-β unsaturated acids by catalytic oxydehydrogenation-esterification of a mixture of an alcohol and a saturated acid as described herein. This results in a more economical and faster process which eliminates the necessity of separately esterifying either the reactants or the products and then separating the esters formed.

SUMMARY OF THE INVENTION

The alkyl α-β unsaturated esters defined herein, for example methyl methacrylate, are formed by contacting an oxydehydrogenation-esterification catalyst defined herein (e.g., an iron, phosphorus, potassium catalyst) with a mixture of oxygen, a saturated acid (e.g., isobutyric acid) and an alkyl alcohol (e.g., methanol) with or without water, preferably with water for a time sufficient to form the alkyl α-β unsaturated ester (e.g., methyl methacrylate).

DESCRIPTION OF THE INVENTION a. General Description of the Process

It was discovered that alkyl α-β unsaturated esters as represented by general formula I, wherein R, $R^1$ and $R^2$ are different or the

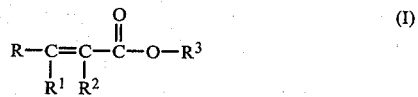

(I)

same and are selected from hydrogen, methyl and ethyl, and $R^3$ is an alkyl of up to ten carbon atoms, are formed by contacting an oxydehydrogenation-esterification catalyst with a feed mixture comprised of a saturated acid represented by general formula II, wherein R, $R^1$ and $R^2$ are different or the same and are as defined

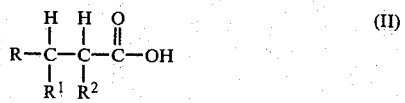

(II)

herein, an alcohol represented by general formula $R_3$—OH, wherein $R_3$ is as defined herein, and oxygen, with or without $H_2O$, for a time sufficient to form an ester of general formula I. R and $R^1$ are preferably methyl or hydrogen with hydrogen being most preferred. $R^2$ is preferably methyl or hydrogen, with methyl being the most preferred. $R^3$ is preferably a straight chained alkyl, with methyl ethyl and n-propyl being the more preferred alkyls and methyl being the most preferred alkyl. Thus the preferred saturated acids are isobutyric acid and propionic acids, and the preferred products are methyl methacrylate and methacrylate.

b. Process Conditions

The mole ratio of alcohol to saturated acid in the feed mixture which contacts the catalyst, varies from five-tenths (0.5) mole to ten (10) moles of alcohol to one (1) mole of saturated acid, but preferably varies from one (1) mole of alcohol to five (5) moles of alcohol per one (1) mole of saturated acid.

The mole ratio of oxygen ($O_2$) to saturated acid in the feed mixture which contacts the catalyst varies from three-tenths (0.3) mole to one and five-tenths (1.5) moles of oxygen per one (1) mole of saturated acid, but preferably varies from five-tenths (0.5) to one (1) mole of oxygen per mole of saturated acid.

Although the feed mixture may contain only oxygen or an alcohol and a saturated acid, it is more preferable to also have water ($H_2O$) in the feed mixture. The term "water ($H_2O$)" refers to steam, liquid, gaseous and/or the vapor state that the molecules of dihydrogen oxygen ($H_2O$) would be in, under the processing conditions described herein. The mole ratio of water to saturated acid in the feed mixture which contacts the catalyst varies from one-tenth (0.1) to forty (40) moles of water to one (1) mole of saturated acid, but preferably it is from five-tenths (0.5) to twenty (20) moles of water per one (1) mole of saturated acid, but the range of from four (4) moles of water to six (6) moles of water per one (1) mole of saturated acid is highly preferred.

The concentration of the saturated acid in the feed will depend upon the catalyst, temperature, pressure, and other variables. The concentration of the saturated acid in the feed is expressed in mole percent and generally varies from one-tenth (0.1) to twenty (20) mole percent. However, a preferable concentration range of the saturated acid in the feed is from about three (3) to six (6) mole percent. The concentration is controlled by the amount of inert gas present in the feed stream. The preferred inert gas is nitrogen, but other gases such as carbon dioxide, helium, argon and the like are suitable. When the concentration of the saturated acid permits, air is a suitable diluted oxidant.

The temperature range of the process described herein may vary from two hundred fifty degrees Centigrade (250° C.) to five hundred fifty degrees Centigrade (550° C.), but preferably it is from three hundred seventy-five degrees Centigrade (375° C.) to four hundred ten degrees Centigrade (410° C.).

The pressure range of the process described herein may vary from one-tenth (0.1) atmosphere (psia) to ten (10) atmospheres (psia), but preferably the pressure is substantially atmospheric pressure, that is, fourteen and seven-tenths (14.7) pounds per square inch absolute (psia) plus or minus ten (10) percent.

The process contact time of the feed mixture with the catalyst will vary with the temperature, pressure, catalyst, and feed mixture, but is sufficient to form one of the alkyl esters of the unsaturated acids defined herein. In general the contact time will vary from two-tenths (0.2) to two (2) seconds, but preferably is from three-tenths (0.3) to one (1) second. The contact time or reaction time is defined as the catalyst volume divided by the gas volume (measured at the reaction temperature) fed per second. The catalyst volume is the bulk volume of the catalyst occupied by the catalyst in the reactor measured at ambient temperature. The term "catalyst"

for bulk volume includes not only the active species of the surface but also the catalyst support as well.

c. Types of Catalysts

The catalysts suitable for the process described herein are heterogeneous oxydehydrogenation-esterification catalysts, that is, they are selective or dual functioning catalysts having sites for oxydehydrogenation of the $\alpha$-$\beta$ hydrogen atoms of the saturated acid, and sites for esterification. A general empirical formula to describe these types of catalysts is $Me.O_x.A_y.N_z$ wherein Me represents a metal atom selected from copper, iron or nickel and mixtures thereof, and A represents an acid anion selected from arsenate $(AsO_4)^{2-}$, borate $(BO_3)^{2-}$, chromate $(CrO_3)^{2-}$, molybdate $(MoO_4)^{2-}$, heteropolyphosphomolybdate $(PMo_{12}O_{42})^{3-}$, heteropolysilicomolybdate $(SiMo_{12}O_{42})^{4-}$, phosphate $(PO_4)^{3-}$, silicate $(SiO_3)^{-3}$, tungstate $(WO_4)^{-2}$, vanadate $(VO_4)^{-2}$ and mixtures thereof. The mixtures being from 0.001 to 1000 mole ratio of one anion to another or one metal atom to another.

In relation to one Me in the catalyst, x represents the number of oxygen atoms (O) required to satisfy the oxidation state of the catalyst, in general it can vary from zero (0) to three (3), and y represents the number of acid anions and generally varies from one hundredth (0.01) to one hundred (100).

N represents an adjuvant atom which assists the catalytic activity of the catalyst and is selected from lithium, sodium, potassium, rubidium, cesium, magnesium, calcium strontium, barium, cobalt, silver, bismuth, tellurium and mixtures thereof. The mixture of adjuvant atoms can vary from 0.001 to 1000 atoms of one adjuvant in relation to another.

z represents zero (0) to twenty (20) N's relative to one (1) Me.

In general the number of acid anions must be in excess of the number of metal atoms or adjuvant atoms. Note the adjuvant atoms may act as promoters, and/or dopants, and/or poison preventers in the catalyst.

The active catalyst may also include support materials which spread out the active catalyst sites, enhance mass and heat transfer and in some cases assist in promoting the catalytic activity of the active catalyst. Some useful supports are silicas and aluminas, molecular sieves, titania and zirconia. It is preferred that acid type supports be used.

In general the catalysts may be described as one or more metal atoms in the form of the metal atom itself, or as an oxide embedded within a matrix of acid anions.

A preferred class of catalysts falling within the useful catalysts described herein are comprised of atoms or iron, phosphorus, oxygen and an adjuvant M and selected from tellurium, cobalt, lanthanum, silver, lithium, sodium, potassium, rubidium, cesium, and mixtures thereof, and are represented by the empirical formula $FeP_{1-2}M_{0.01-1}O_x$ wherein relative to one atom of iron, the relative number of atoms of phosphorus is from one (1) to two (2), the relative number of M's is from one hundredth (0.01) to one (1) and x represents the number of oxygen atoms required to satisfy the valence states, that is, the oxidation state of the catalyst. It is highly preferred that M be lithium, sodium, potassium, rubidium or cesium, and it is especially preferred that M be cesium.

d. Method of Preparing the Catalysts Described Herein

A number of techniques for preparing the catalysts useful in the practice of this invention are known to those skilled in the art. Of these, the more facile methods involve preparing the integral composition prior to calcination. This is accomplished by employing the so-called slurry method or the precipitation method. In the precipitation method an aqueous solution of salts of the contemplated metals and phosphoric acid is prepared then neutralized with an appropriate base to precipitate the mixed metal phosphates. The precipitate is carefully washed to remove all traces of water solubles and then dried prior to calcining. In the alternative, one can add ammonium phosphate to the solution of metal salts to precipitate directly the metal phosphates. Although any water-soluble salt of iron or silver can be used, nitrate salts are preferred.

The so-called slurry method is more convenient to carry out and is the preferred method. In this procedure, an aqueous solution of the metals salts and phosphoric acid is prepared, and then the solution is heated with stirring to remove water. Heating is continued until the mass can no longer be stirred. The residue is then fragmented and again heated at a moderately elevated temperature of about one hundred twenty degrees Centigrade (120° C.) until completely dried. The completely dried composite is sized to about twelve to fifteen mesh size and calcined. Suitable calcination temperatures broadly range from four hundred to five hundred fifty degrees Centigrade (400°–550° C.). Applicable calcination periods range from two (2) to sixteen (16) hours.

A suitable supported catalyst can be prepared by either of these techniques. For example, in the slurry method, colloidal silica or any other form of silica as well as other supports such as alumina, quartz, titanium dioxide, molecular sieves, etc., can be added prior to removing the water content. Similarly, in the precipitation method described, the metal phosphates can be precipitated in the presence of suspended particulates of the intended support.

e. Examples of Catalysts Prepared as Described Herein

EXAMPLE I

This example illustrates the slurry method for preparing a supported lanthanum doped iron phosphate catalyst useful in the practice of this invention.

Iron nitrate nonahydrate in the amount of 404.0 g along with 86.2 g of lanthanum nitrate, hexahydrate and 140 g of phosphoric acid were dissolved in 400 ml of distilled water. The solution of metal salts and acid was mixed with 100 ml of LUDOX 40 HS and stirring continued at 85° C. until the bulk of the water had been evaporated. The resultant paste was further dried at 120° C. until in condition to be sized whereupon drying was continued for 6 hours. The dried particulates were then calcined at 450° C. for 6 hours and used in the form of 12-15 mesh sizes. The gram-atom empirical formula of the calcined composition follows: $FeP_{1.44}La_{0.20}O_x/20\% SiO_2$.

EXAMPLE II

In a manner similar to that described in Example I a cobalt doped iron phosphate catalyst composition was prepared. The gram-atom empirical formula of the resultant compositions follows: $FeP_{1.44}Co_{0.1}O_x/3.5\% SiO_2$.

EXAMPLE III

Iron nitrate nonahydrate in the amount of 404.4 g along with 8.02 g of tellurium dioxide and 127.16 g of phosphoric acid were dissolved in 400 ml of distilled water. One hundred milliliters of silica gel containing 40% $SiO_2$ were added to the resultant solution. The solution was then stirred at 85° C. until the bulk of the water had been evaporated. The resultant paste was further dried at 120° C. until in condition to be fragmented whereupon drying was continued for 12 hours. The dried mixture was calcined at 450° C. for 6 hours. The gram-atom empirical formula of the calcined composition follows: $FeP_{1.3}Te_{0.05}O_x$.

EXAMPLE IV

A catalyst was prepared as in Example III, except that iron nitrate nonahydrate in the amount of 103.21 g along with 7.47 g of silver nitrate were dissolved in 200 ml of distilled water. Concentrated phosphoric acid in the amount of 35.8 g together with 30.0 cc of silica gel containing 20% colloidal $SiO_2$ were added to the solution of the metal salts. The solution was then stirred at 85° C. until the bulk of the water had been evaporated. The resultant paste was further dried at 120° C. until in condition to be fragmented whereupon drying was continued for 12 hours at 150° C. The dried mixture was calcined at 450° C. for 16 hours and for an additional 2 hours at 520° C. The gram-atom empirical formula of the calcined mixed phosphates of iron and silver follows: $FeP_{1.44}Ag_{0.176}O_x$.

EXAMPLE V

A further catalyst system was prepared as in Example IV wherein no support was employed. The gram-atom empirical formula of the resultant mixed phosphates of iron and silver follows: $FeP_{1.44}Ag_{0.16}O_x$.

EXAMPLE VII

A catalyst was prepared by the slurry method as described in Example IV, except that 112.25 g of iron nitrate nonahydrate, 200 ml of distilled water, 5.6208 g of potassium nitrate and 22.5 ml of concentrated (85 weight percent) phosphoric acid and 40 ml of colloidal silica containing 20 weight percent $SiO_2$ were used. The dried calcined mass was crushed to 12–15 mesh sieve size particles. Its gram-atom empirical formula was $FeP_{1.432}K_{0.2}O_x/25\%\ SiO_2$.

EXAMPLE VIII

A catalyst without a support was prepared by the slurry method as described in Example IV except that 420 g of iron nitrate-nonahydrate, 48.5 g of bismuth nitrate, 40.8 g of potassium nitrate, 200 ml of distilled water, and 471.4 g of ammonium phosphate dissolved in 500 ml of distilled water was used. The dried calcined mass was crushed to 12–15 mesh sieve size particles. Its empirical gram-atom formula was $FeP_{1.715}Bi_{0.095}K_{0.38}O_x$.

Use of the Catalyst in the Processes Described Herein

The catalyst compositions of this invention can be employed in a fluidized reactor, stirred tank reactor, or fixed-bed type reactor. Because of the convenience associated with the use of a fixed-bed reactor in a small scale operation, such a reactor will be exemplified herein. In the preferred mode of operation of feed to the reactor comprises a pre-heated gaseous mixture of the saturated acid, alcohol, molecular oxygen, steam and inert diluent gas. A pre-heat temperature in the range of about 300° to 350° C. is customarily used. A broad range of applicable reaction temperatures is from 300°–500° C. but more generally a temperature of from 375° to 425° C. provides for optimum processing.

Examples of the Process Described Herein

These examples illustrate the process described herein for the catalytic oxydehydrogenation-esterification of isobutyric acid and methanol as well as illustrating the like conversion of other compounds described herein. The reactor and the general manner of conducting the reaction was the same for each of the enumerated runs.

The procedure observed consisted of feeding a preheated (350° C.) mixture of the applicable saturated acid, alcohol, oxygen, nitrogen and steam through a stainless steel tube of ½" OD (⅜" ID) and approximately 18" in length containing the test catalyst as a 15 cc packed bed maintained at the reaction temperature utilized in the particular run.

The pre-heater consisted of a length of stainless steel tube similar to the reactor but packed with glass beads.

The products were collected and any carbon dioxide formed in the course of reaction was absorbed in an Ascarite tube protected by a calcium chloride absorber for any uncondensed water. The condensed organic product was separated from the water, collected and analyzed by the internal standard method of gas chromatography.

A feed mixture consisting of isobutyric acid/methanol/water/oxygen/nitrogen in the molar ratio of 1/4.4/5.1/0.8/22.5, at 0.57 seconds contact time at the reaction temperature of 410° C., and at atmospheric pressure (14.7 psia) was passed through a catalyst bed containing 15.0 cc of a 12–15 mesh particles of catalyst of $FeP_{1.432}K_{0.2}O_x/25$ weight percent $SiO_2$ (from Example VII) for one hour, to give 99 percent conversion, with a selectivity to methyl isobutyrate of 12.32 percent, to methyl methacrylate of 45.65 percent, and to methacrylic acid of 28.32 percent. The methanol recovery in this process was 85.6 mole percent, after subtracting the methanol which reacted to form the esters.

EXAMPLE X

A feed mixture consisting of isobutyric acid/methanol/oxygen/nitrogen in the molar ratio of 1/6.6/0.8/22.5 at a contact time of 0.63 seconds and at a reaction temperature of 390° C. and at atmospheric pressure was passed through a catalyst bed containing 15.0 cc of 12–15 mesh particles of catalyst of $FeP_{1.715}Bi_{0.095}K_{0.38}O_x$ (from Example VIII) for one hour to give 89.0 percent conversion, and a selectivity to methyl isobutyrate of 42.54 percent, to methyl methacrylate. 17.55 percent, and to methacrylic acid of 34.04 percent. The methanol recovery in this process was 85.6 mole percent after subtracting the methanol which reacted to form the esters.

The following examples illustrate the necessity for the use of the catalysts described herein.

EXAMPLE XI

A feed mixture of isobutyric acid/water/oxygen/nitrogen at a molar ratio of 1/2.58/0.8/15.6 was passed at atmospheric pressure, at a contact time of 0.47 seconds at 330° C. through 15 cc bed of 12–15 mesh particles of catalyst having a gram-atom empirical formula $Sb_{1.0}P_{1.0}Mo_{12.0}O_x/15.1$ weight percent $TiO_2$ for one hour to give 46.5 percent conversion of isobutyric acid with a 64 percent selectivity to methacrylic acid.

The catalyst is described in U.S. Pat. No. 4,212,767 and was prepared by the slurry method in which 212 g of ammonium molybdate was dissolved in 500 ml of distilled water. Then 10.8 g of phosphoric acid and 22.8 g of antimony trichloride were added and the slurry after mixing was dried at 120° C. for 16 hours and then calcined at 350° C. for 15 hours. The calcined mixture was crushed or sieved, and the 12-15 mesh sizes were used.

EXAMPLE XII

A feed mixture of isobutyric acid/methanol/oxygen/nitrogen at molar ratio of 1/2.5/0.81/7.0 was passed through the bed of catalyst particles (as described in Example XI) except that the contact time was 0.58 seconds and the reaction temperature was 320° c. The conversion of isobutyric acid was 72 percent, with a selectivity to methyl isobutyrate of 90±3 percent, a selectivity to methacrylic acid of 6 percent, and a selectivity to methyl methacrylate of less than one (1) percent.

As used herein, the percent conversion is defined as:

$$\% \text{ Conversion} = \frac{\text{moles of IBA fed} - \text{moles of IBA recovered}}{\text{moles of IBA fed}} \times 100\%$$

The percent selectivity of a compound is defined as:

$$\% \text{ Selectivity} = \frac{\text{moles of compound formed}}{\text{moles IBA fed} - \text{moles IBA recovered}} \times 100\%$$

p0 The contact time is defined at the reaction temperature as:

$$\text{Contact Time} = \frac{\text{cc of catalyst bed}}{\text{total feed cc/hr}} \times \frac{3600 \text{ sec}}{\text{hour}} \times \frac{293° \text{ K.}}{T_R}$$

$T_R$ = reaction temperature in degrees Kelvin (°K.)

The total feed is defined as:

Total feed = sum of the reactants, water, nitrogen and other diluents such as $CO_2$, helium or argon, expressed in cc per hour at 293° K.

Although the invention has been described herein with reference to specific details of certain illustrative embodiments, it is not intended that the invention shall be limited thereby, except insofar as such details appear in the accompanying claims.

We claim:

1. A process for forming alkyl α-β unsaturated esters of general formula I

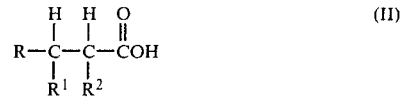

wherein R, $R^1$ and $R^2$ are different or the same and are selected from hydrogen, methyl and ethyl; and $R^3$ is an alkyl of up to ten (10) carbon atoms, which comprises contacting an oxydehydrogenation-esterification catalyst having sites for oxydehydrogenation of the α-β hydrogen atoms of the saturated acid and for esterification with a feed mixture comprised of a saturated acid of general formula II

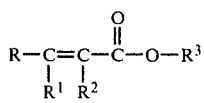

wherein R, $R^1$ and $R^2$ are different or the same and are as defined, an alcohol of general formula $R^3$—OH wherein $R^3$ is as defined, and oxygen, for a time sufficient to form an ester of general formula I.

2. The process as defined in claim 1 wherein the mole ratio of alcohol to saturated acid in the feed mixture is from one (1) mole of alcohol to five (5) moles of alcohol per mole of saturated acid, the mole ratio of oxygen to saturated acid in the feed mixture is from five-tenths (0.5) moles to one (1) mole of oxygen per mole of saturated acid, and the concentration of the saturated acid in the feed is from three (3) to six (6) mole percent.

3. The process as defined in claim 2 wherein the temperature is from two hundred fifty degrees Centigrade (250° C.) to five hundred fifty degrees Centigrade (550° C.)

4. The process as defined in claim 3, wherein the pressure is from one-tenth (0.1) atmosphere (psia) to ten (10) atmospheres (psia).

5. The process as defined in claim 4, wherein the contact time is from two-tenths (0.2) to two (2) seconds.

6. The process as defined in any of claims 1, 2, 3, 4, or 5 wherein the feed mixture is further comprised of water, the mole ratio of water to saturated acid is from five-tenths (0.5) to twenty (20) moles per mole of saturated acid.

7. The process as defined in any of claims 1, 2, 3, 4, or 5 wherein the catalyst is comprised of a metal atom represented by Me and selected from the group consisting of copper, iron, nickel and mixtures thereof, and an acid anion represented by A and selected from the group consisting of arsenate $(AsO_4)^{2-}$, Borate $(BO_3)^{2-}$, chromate $(CrO_3)^{2-}$, molybdate $(MoO_4)^{2-}$, heteropolyphosphomolybdate $(PMo_{12}O_{42})^{3-}$, heteropolysilicomolybdate $(SiMo_{12}O_{42})^{4-}$, phosphate $(PO_4)^{3-}$, silicate $(SiO_3)^{3-}$, tungstate $(WO_4)^{-2}$, vanadate $(VO_4)^{-2}$ and mixtures thereof, said catalyst being represented by the general empirical formula:

wherein relative to one (1) Me in the catalyst, x represents the number of oxygen atoms required to satisfy the oxidation state of the catalyst; y represents one hundredth (0.01) to one hundred (100) anions represented by A relative to one (1) Me in the catalyst; N represents an adjuvant which assists the catalytic activity of the catalyst and is selected from lithium, sodium, potassium, rubidium, cesium, magnesium, calcium, strontium, barium, cobalt, silver, bismuth, tellurium and mixtures thereof; and z represents zero (0) to twenty (20) N's relative to one (1) Me.

8. The process as defined in claim 6 wherein the catalyst is comprised of a metal atom represented by Me and selected from the group consisting of copper, iron, nickel and mixtures thereof, and an acid anion represented by A and selected from the group consisting of arsenate $(AsO_4)^{2-}$, borate $(BO_3)^{2-}$, chromate $(CrO_3)^{2-}$, molybdate $(MoO_4)^{2-}$, heteropolyphosphomolybdate $(PMo_{12}O_{42})^{3-}$, heteropolysilicomolybdate $(SiMo_{12}O_{42})^{4-}$, phosphate $(PO_3)^{3-}$, silicate $(SiO_3)^{3-}$, tungstate $(WO_4)^{-2}$, vanadate $(VO_4)^{-2}$ and mixtures thereof, said catalyst being represented by the general empirical formula:

$$Me.O_x.A_y.N_z$$

wherein relative to one (1) Me in the catalyst, x represents the number of oxygen atoms required to satisfy the oxidation state of the catalyst; y represents one hundredth (0.01) to one hundred (100) anions represented by A relative to one (1) Me in the catalyst; N represents an adjuvant which assists the catalytic activity of the catalyst and is selected from lithium, sodium, potassium, rubidium, cesium, magnesium, calcium, strontium, barium, cobalt, silver, bismuth, tellurium and mixtures thereof; and z represents zero (0) to twenty (20) N's relative to one (1) Me.

9. The process as defined in any of claims 1, 2, 3, 4 or 5 wherein the catalyst is comprised of iron, phosphorus, and an adjuvant selected from the group consisting of lithium, sodium, potassium, rubidium, cesium, lanthanum, cobalt, silver and tellurium, and is represented by the empirical formula $FeP_{1-2}M_{0.01-1}O_x$ wherein relative to one (1) atom of iron, phosphorus is from one (1) to two (2); M represents the adjuvant, and is from one hundredth (0.01) to one (1); and x represents the number of oxygen atoms required to satisfy the oxidation state of the catalyst.

10. The process as defined in claim 6, wherein the catalyst is comprised of iron, phosphorus, and an adjuvant selected from the group consisting of lithium, sodium, potassium, rubidium, cesium, cobalt, lanthanum, silver and tellurium, and is represented by the empirical formula $FeP_{1-2}M_{0.01-1}O_x$ wherein relative to one (1) atom of iron, phosphorus is from one (1) to two (2); M represents the adjuvant, and is from one hundredth (0.01) to one (1); and x represents the number of oxygen atoms required to satisfy the oxidation state of the catalyst.

11. The process as defined in claim 10 wherein the temperature is from three hundred seventy-five degrees Centigrade (375° C.) to four hundred ten degrees Centigrade (410° C.), the pressure is substantially at atmospheric pressure, the mole ratio of $H_2O$ to acid is from four (4) to six (6) moles of $H_2O$ to one (1) mole of acid, the contact time is from three-tenths (0.3) to one (1) second and the mole percent of the saturated acid is from three (3) to six (6) percent.

12. The process as defined in any of claims 1, 2, 3, 4 or 5 wherein the acid is selected from the group consisting of isobutyric acid and propionic acid, and the alcohol is methanol.

13. The process as defined in claim 6 wherein the acid is selected from the group consisting of isobutyric acid and propionic acid, and the alcohol is methanol.

14. The process as defined in claim 7 wherein the acid is selected from the group consisting of isobutyric acid and propionic acid, and the alcohol is methanol.

15. The process as defined in claim 8 wherein the acid is selected from the group consisting of isobutyric acid and propionic acid, and the alcohol is methanol.

16. The process as defined in claim 9 wherein the acid is selected from the group consisting of isobutyric acid and propionic acid, and the alcohol is methanol.

17. The process as defined in claim 10 wherein the acid is selected from the group consisting of isobutyric acid and propionic acid, and the alcohol is methanol.

18. The process as defined in claim 11 wherein the acid is selected from the group consisting of isobutyric acid and propionic acid, and the alcohol is methanol.

19. The process as defined in any of claims 1, 2, 3, 4 or 5 wherein the acid is isobutyric acid and the alcohol is methanol.

20. The process as defined in claim 6 wherein the acid is isobutyric acid and the alcohol is methanol.

21. The process as defined in claim 7 wherein the acid is isobutyric acid and the alcohol is methanol.

22. The process as defined in claim 8 wherein the acid is isobutyric acid and the alcohol is methanol.

23. The process as defined in claim 9 wherein the acid is isobutyric acid and the alcohol is methanol.

24. The process as defined in claim 10 wherein the acid is isobutyric acid and the alcohol is methanol.

25. The process as defined in claim 11 wherein the acid is isobutyric acid and the alcohol is methanol.

* * * * *

UNITED STATES PATENT AND TRADEMARK OFFICE
CERTIFICATE OF CORRECTION

PATENT NO. : 4,331,813

DATED : May 25, 1982

INVENTOR(S) : Chelliah Daniel and Phyllis L. Brusky

It is certified that error appears in the above-identified patent and that said Letters Patent is hereby corrected as shown below:

On the title page item [75] Inventors:

"Phillis L. Brusky" should read --Phyllis L. Brusky--.

Column 7, line 34, delete "$p^O$".

Signed and Sealed this

Thirtieth Day of November 1982

[SEAL]

Attest:

Attesting Officer

GERALD J. MOSSINGHOFF

Commissioner of Patents and Trademarks